United States Patent [19]

Tafesh et al.

[11] Patent Number: 5,393,924
[45] Date of Patent: Feb. 28, 1995

[54] METHOD FOR THE PREPARATION OF ARYLALKANOLAMINEACYLATES

[75] Inventors: Ahmed M. Tafesh, Corpus Christi, Tex.; Olan S. Fruchey, Bad Soden/T.S., Germany; Charles B. Hilton, Corpus Christi, Tex.

[73] Assignee: Hoechst Celanese Corporation, Somerville, N.J.

[21] Appl. No.: 235,582

[22] Filed: Apr. 29, 1994

Related U.S. Application Data

[62] Division of Ser. No. 913,124, Oct. 2, 1992, Pat. No. 5,338,884.

[51] Int. Cl.$^6$ .......................................... C07C 231/00
[52] U.S. Cl. ................................. 564/138; 562/490; 562/577; 562/606; 562/503; 562/498; 562/504; 562/505; 562/506; 562/508
[58] Field of Search .............. 564/138; 562/490, 577, 562/606, 503, 498, 504, 505, 506, 508

[56] References Cited

U.S. PATENT DOCUMENTS

| | | | |
|---|---|---|---|
| 1,995,709 | 9/1931 | Hartung et al. | 564/138 |
| 2,567,906 | 9/1951 | Hartung et al. | 564/138 |
| 3,966,813 | 6/1976 | Satzinger et al. | 564/138 |
| 5,338,884 | 8/1994 | Tafesh et al. | 564/138 |

*Primary Examiner*—Raymond Henley, III
*Assistant Examiner*—Keith MacMillan
*Attorney, Agent, or Firm*—James J. Mullen; Donald R. Cassady

[57] ABSTRACT

Acylamides or amine acylate salts of arylalkanolamines are prepared by reacting an arylisonitrosoalkanone with hydrogen and a carboxylic acid, carboxylic acid anhydride or carboxylic acid ester or mixture thereof in the presence of a transition metal catalyst; optionally the product is converted to the corresponding arylalkanolamine hydrochloride salt by reaction of the acylamide or amine acylate salt of the arylalkanolamine with hydrogen chloride in a $C_1$-$C_3$ alkyl alcohol.

18 Claims, No Drawings

METHOD FOR THE PREPARATION OF ARYLALKANOLAMINEACYLATES

This application is a divisional of application Ser. No. 07/913,124, filed on Oct. 2, 1992, now U.S. Pat. No. 5,338,884.

BACKGROUND OF THE INVENTION

1. Field of the Invention

This invention relates to a method for the conversion of substituted or unsubstituted arylisonitrosoalkanones to acyl amides, the amine acylate salts of substituted or unsubstituted arylalkanolamines and the hydrolysis hydrochloride salts thereof. In a very particular aspect, this invention relates to 1-(o- or p-hydroxphenyl)-ethan-1-ol-2-acetamide and 1-(o- or p-hydroxyphenyl)-ethan-1-ol-2-amine acetate, methods of their preparation and their hydrochloride hydrolysis salts.

2. Background Art

Substituted and unsubstituted arylalkanolamines are chemical intermediates of great importance. They are used in the preparation of pharmacologically active compounds and in some instances are themselves pharmacologically active. For example, p-hydroxyphenylethanolamine (octopamine) is a sympathomimetic which produces vasoconstricting and cardiotonic effects.

In U.S. Pat. Nos. 1,995,709 and 2,567,906 by Hartung, a multi-operations procedure for the preparation of substituted phenylpropanolamines is described, particularly, for 1-(p- or m-hydroxyphenyl)-2-amino-1-propanol (in U.S. Pat. No. 1,995,709), and 1-(p-aminophenyl)-2-amino-1-propanol (in U.S. Pat. No. 2,507,906). In U.S. Pat. No. 1,995,709, p- or m-hydroxypropiophenone is reacted with a lower alkyl nitrite in ether in the presence of hydrogen chloride to produce p- or m-hydroxyisonitrosopropiophenone, which then is separated from the reaction mixture by alkaline extraction and recovered from the alkaline solution by precipitation induced by acidification of the extract, after which the precipitate is recrystallized. The p- or m-hydroxyisonitrosopropiophenone thus separated is then reacted with hydrogen in the presence of palladium on charcoal in absolute alcohol containing dry hydrogen chloride until reduction stops, after which the amino ketone is recovered as a filtrate. The filtrate is dried and purified by recrystallization. Then the amino ketone is dissolved in water and reacted with hydrogen in the presence of palladium on charcoal. The reaction product is recovered as the hydrochloride of the amino alcohol, for example, the hydrochloride of 1-(p-hydroxyphenyl)-2-aminopropanol (in U.S. Pat. No. 1,995,709) and the hydrochloride of 1-(p-aminophenyl)-2-aminopropanol (in U.S. Pat. No. 2,507,906).

In U.S. Pat. No. 2,505,645 by McPhee, the acidic catalytic hydrogenation process described by Hartung is employed in a method of preparing α-phenyl-β-hydroxphenyl-β-hydroxyethylamine.

U.S. Pat. No. 2,784,228 by Hartung describes an also partially aqueous alternative process for the catalytic reduction of α-oximino ketones, using alkaline solutions instead of acidic solutions to obtain a desired amino alcohol. Difficulties and shortcomings of the acidic catalytic reduction process described by Hartung in U.S. Pat. Nos. 1,995,709 and 2,567,906 are detailed by Hartung in U.S. Pat. No. 2,784,228 and also by Wilbert et at. in U.S. Pat. No. 3,028,429. In U.S. Pat. No. 3,028,429, Wilbert et al. describe a process for the hydrogenation of isonitrosopropiophenone to produce 1-phenyl-2-aminopropanol which is a modification said to improve yields respecting the general process described by Hartung in U.S. Pat. Nos. 1,995,709 and 2,567,906.

U.S. Pat. No. 3,966,813 by Satzinger et al. claims a process for preparation of 1-(hydroxyphenyl)-2-aminoethanol (octopamine) by reacting a hydroxyacetophenone with a lower alkyl nitrite in a dipolar aprotic solvent in the presence of a hydrogen chloride catalyst to form isonitrosoacetophenone, and then catalytically hydrogenating the isonitrosoacetophenone in the presence of palladium to reduce the isonitroso and keto moieties on the isonitrosoacetophenone molecule. Satzinger, et al. provide several examples for the preparation of both m-hydroxyisonitrosoacetophenone and p-hydroxyisonitrosoacetophenone. However, only one example (Example 4) describes the hydrogenation step for conversion of an hydroxyisonitrosoacetophenone to a 1-(hydroxyphenyl)-2-aminoethanol. Example 4 pertains to hydrogenation of the meta substituted m-hydroxyisonitrosoacetophenone. On the basis of Example 4, Satzinger, et al. propose and claim that the para substituted p-hydroxyisonitrosoacetophenone can also be converted by the same hydrogenation step to the aminoethanol.

However, it has been discovered in the laboratories of the assignee of this invention that hydrogenation of the p-hydroxyisonitrosoacetophenone does not produce the proposed aminoethanol; instead, p-hydroxyphenethylamine (tyramine) is produced. The controlling feature appears to be the fact that the presence of a hydroxyl group at the ortho and/or para position strongly activates the benzylic carbon toward hydrogenolysis, but the presence of a hydroxyl group at the meta position on the hydroxyisonitrsoacetophenone is unable to activate the benzylic carbon toward hydrogenolysis. The unactivated benzylic carbon affects the hydrogenation reaction so that an aminoethanol is formed. The strongly activated benzylic carbon affects the hydrogenation reaction so that an ethylamine is formed. Since both para substitution and ortho substitution strongly activate the benzylic carbon, the ethylamine is formed when a hydroxyl group is present at either or both of these substitution positions.

SUMMARY OF THE INVENTION

An object of this invention is the preparation of acylamides and amine acylate salts of arylalkanolamines.

An object of this invention is the preparation of hydrochloride salts of arylalkanolamines from acylamides and amine acylate salts of arylalkanolamines.

An object of this invention is the use of arylisonitrosoalkanones wherein the aryl group is unsubstituted or is substituted in the ortho and/or para position, to prepare acylamides and amine acylate salts of arylalkanolamines, in a hydrogenation method employing a transition metal catalyst.

An object of this invention is a method for the production of acylamides and amine acylate salts of arylalkanolamines under mild conditions of temperature and pressure.

An object of this invention is a method wherein a solvent medium is a reactant for the production of acylamides and amine acylate salts of arylalkanolamines.

An object of this invention is a method for the production of acylamides and amine acylate salts of arylalkylamines involving hydrogenation wherein the hydrogenation can be conducted without controlling the amount of hydrogen introduced to the reaction mixture.

An object of this invention is the preparation and provision of 1-(o- or p-hydroxyphenyl)-ethan- 1-ol-2-amine acetate.

An object of this invention is the preparation and provision of 1-(o- or p-hydroxyphenyl)-ethan- 1-ol-2-acetamide.

An object of this invention is a method of convening 1-(o- or p-hydroxyphenyl)-ethan-1-ol-2-acetamide to the hydrochloride salt of 1-(o- or p-hydroxyphenyl)-2-amino ethanol.

An object of this invention is a method of converting 1-(o- or p-hydroxyphenyl)-ethan-1-ol-2-amine acetate to the hydrochloride salt of 1-(o- or p-hydroxyphenyl)-ethan- 1-ol-2-amine.

In accordance with the present invention, a method for the preparation of an acylamide or amine acylate salts of an arylalkanolamine is disclosed, the method comprising the steps of:

a) providing a compound of the formula

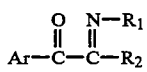

wherein
$R_1$ = an hydroxyl, alkyl, or alkyloxy radical
$R_2$ = hydrogen or a $C_1$-$C_8$ alkyl r cycloalkyl radical, and
Ar = an unsubstituted phenyl radical, or a phenyl radical substituted at the ortho and/or para position; or a naphthyl radical unsubstituted, or substituted at one or more of the 1, 3, 6, and 7 positions; wherein one or more substituents are selected from the group consisting of hydroxyl, alkoxy, alkyl, phenyl, and benzyl radicals, wherein the alkyl component is a branched or unbranched $C_1$-$C_8$ alkyl radical, wherein any alkyl, phenyl and benzyl radicals are optionally substituted with one or more substituents selected from hydroxyl, sulfonic acid, and sulfonic acid radicals, and wherein said phenyl and benzyl substituents are optionally substituted with a $C_1$-$C_8$ alkyl or $C_1$-$C_8$ alkoxy radical, or both; and b) reacting said compound with hydrogen in a reaction medium comprising an acyl donor selected from carboxylic acids, carboxylic acid anhydrides and esters of a carboxylic acid in the presence of transition metal catalyst to produce a reaction product comprising, as its major component, either the carboxylic acid salt of an arylalkanolamine if said selected acyl donor is a carboxylic acid, or the amine acylate salt of an arylalkanolamine if said selected acyl donor is said anhydride or ester.

The acyl donor may generally be described according to the formula

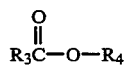

wherein
$R_3$ = hydrogen or an alkyl, cycloalkyl, aryl or arylalkyl having from 1 to 10 carbon atoms, and
$R_4$ = hydrogen, —$OCR_3$ or —$R_3$ (wherein $R_3$ has the same meaning as above.

The acylamide of an arylalkanolamine of this invention has the formula

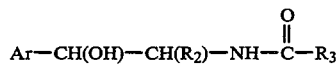

wherein $R_2$, $R_3$ and Ar have the same meaning as above.

The amine acylate salt of an arylalkanolamine of this invention has the formula

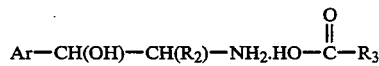

wherein $R_2$, $R_3$ and Ar have the same meaning as above.

In the method of this invention the reaction medium preferably comprises at least one mole equivalent of the acyl donor per mole of the arylisonitrosoalkanone, and hydrogen is provided in sufficient quantity for reaction of 3 mole equivalents of hydrogen in the conversion of the arylisonitrosoalkanone to the acylamide or amine acylate salt of an arylalkanolamine. Thus, stoichiometrically, where the acyl donor is a carboxylic acid anhydride or ester (i.e., where $R_4$, is not hydrogen), the reaction may be depicted as

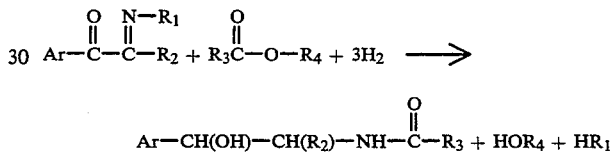

Where the acyl donor is a carboxylic acid ($R_4$ is hydrogen), the reaction is

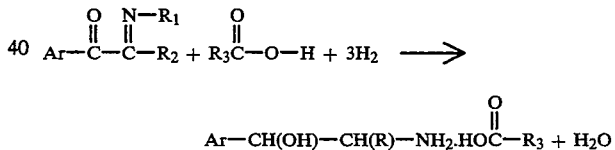

The transition metal catalyst is supported on an inert support, and suitably is provided in an mount of from about 0.005% to about 1.5% by weight based on the amount of the arylisonitrosoalkanone compound. The transition metal is selected from the group consisting of platinum, palladium, nickel, rhodium, and combinations thereof, and preferably is palladium on a carbon support. The reaction is carried out under hydrogen pressure ranging from about 15 psig to about 300 psig, at temperatures ranging from 5° C. to about 100° C.

DETAILED DESCRIPTION OF THE INVENTION

In accordance with this invention, good yields of the acylamide or amine acylate salts of substituted and unsubstituted arylalkanolamines are obtained by hydrogenating arylisonitrosoalkanones, wherein the aryl group is unsubstituted or is substituted at the ortho and/or para position, in the presence of a supported transition metal catalyst in a reaction medium comprising an acyl donor selected from carboxylic acids, carboxylic acid anhydrides, esters of carboxylic acids, or mixtures thereof.

Typically the conversion of the arylisonitrosoalkanone of the formula disclosed above to the acylamide or amine acylate salt of an arylalkanolamine, using the method of the present invention, results in a yield ranging from about 40% to about 95% based on the arylisonitrosoalkanone.

More particularly, the acylamide or amine acylate salts of substituted and unsubstituted arylalkanolamines are obtained by reacting about one molar equivalent of the acyl donors based on the quantity of arylisonitrosoalkanone, wherein the ketone is present in a quantity ranging from about 5% by weight to about 50% by weight, preferably from about 5% by weight to about 30% by weight, of the reaction medium, and wherein the reaction medium comprises from about 5% by weight to about 90% by weight of the acyl donor, and wherein the reaction is carried out in the presence of a transition metal on an inert substrate (typically carbon), wherein the overall catalyst composition comprises from about 5% by weight to about 25% by weight, preferably from about 5% by weight to 10% by weight of the transition metal, and wherein the catalyst is present in quantity sufficient to provide from about 0.005% by weight to about 5.0% by weight, preferably from about 0.001% by weight to about 1.5% by weight, of the transition metal based on weight of the arylisonitrosoalkanone. (The reaction medium excludes the arylisonitrosoalkanone, but includes the transition metal catalyst and the acyl donor.)

When the reaction medium comprises a carboxylic acid, the carboxylic acid comprises from about 5% by weight to about 95% by weight of the reaction medium, and more preferably from about 40% by weight to about 90% by weight of the reaction medium.

The substituted and unsubstituted arylisonitrosoalkanone employed in the invention has the formula

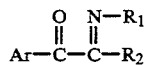

in which $R_1$ represents a hydroxyl, $C_1$-$C_8$ alkyl or alkyloxy radical and $R_2$ represents hydrogen or a $C_1$-$C_8$ alkyl or cycloalkyl radical, and Ar represents an aromatic phenyl radical unsubstituted, or substituted at the ortho and/or para position, or naphthyl radical unsubstituted or substituted at one or more of the 1, 3, 6, and 7 positions, with one or more substituents selected from the group consisting of hydroxyl, alkoxy, alkyl, phenyl, benzyl, and aryloxy radicals, wherein the alkyl in the alkyl-containing substituent(s) is a branched or unbranched $C_1$-$C_8$ alkyl radical and any of such alkyl and the phenyl and benzyl radicals may be optionally substituted with one or more substituents selected from hydroxyl, sulfonic acid, and sulfinic acid radicals, the phenyl and benzyl substituents also or alternatively being optionally substituted with one or more $C_1$-$C_8$ alkyl or $C_1$-$C_8$ alkoxy, or both, radicals.

The acyl donor used in this invention is a carboxylic acid, a carboxylic acid anhydride, a carboxylic ester, or a mixture of them, and is generally described by the formula

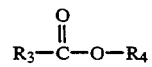

wherein $R_3$ is an alkyl, cycloalkyl, aryl, or arylalkyl having from 1 to 10 carbon atoms, and $R_4$ is hydrogen, —$OCR_3$ or $R_3$ with $R_3$ meaning the same as before. Thus, the acyl donor may be a carboxylic acid such as acetic acid, propanoic acid, butanoic acid, pentanoic acid, hexanoic acid, heptanoic acid, octanoic acid, nonanoic or decanoic acid; a carboxylic acid anhydride such as acetic anhydride, propanoic anhydride, butanoic anhydride, acetic propanoic anhydride; and carboxylic acid esters such as methyl acetate, ethyl acetate, n-propyl acetate, isopropyl acetate, n-butyl acetate, sec-butyl acetate, isobutyl acetate, amyl acetate, sec-amyl acetate, methyl amyl acetate, 2-ethyl butyl acetate, cyclohexyl acetate, methyl cyclohexanyl acetate, ethylene glycol monoacetate, glycol diacetate, ethylene glycol monoethyl ether acetate, methoxy butyl acetate, methyl propionate, ethyl propionate, n-butyl propionate, amyl propionate, ethyl butyrate, methyl butyrate, n-butyl butyrate, ethyl hyroxy-iso-butyrate, diethyl carbonate, methyl formate, ethyl formate, butyl formate, amyl formate, methyl lactate, ethyl lactate, and butyl lactate. The acyl donor is liquid at the temperature and pressures employed and has a melting point not exceeding 100° C. and a boiling point in excess of the reaction temperature employed. Normally suitably the boiling point will be above 100° C. (at one atmosphere). The preferred acyl donor is acetic acid.

Hydrogenation of the substituted or unsubstituted arylisonitrosoalkanone is carried out using hydrogen in the presence of a transition metal hydrogenation catalyst selected from the group consisting of platinum, palladium, nickel, and rhodium or mixtures thereof on an inert support. The inert support typically comprises carbon or barium sulfate; the hydrogenation catalyst comprises from about 1% by weight to about 25% by weight of the combination including hydrogenation catalyst and inch support. The preferred inert support material is carbon, and the most preferred hydrogenation catalyst comprises palladium on carbon, wherein the palladium comprises from about 5% by weight to about 25% by weight of the combination of palladium on carbon, as previously disclosed.

The hydrogenation is conducted under positive hydrogen pressures of from about 15 to about 300 psig, preferably in the range from about 30 to about 100 psig at temperatures suitably in the range from about 5° C. to about 100° C., preferably in the range from about 10° C. to about 50° C. At temperatures in the upper part of the useful range, the α-oximinoketone conversion to the acylamide or amine acylate salt of the arylalkanolamine proceeds very rapidly and, generally speaking, better reaction control is realized in the preferred temperature range.

In preferred embodiments, 1-(o- or p-hydroxyphenyl)-ethan-1-ol-2-acetamide (octopamine acetate) or 1-(o- or p-hydroxyphenyl)-ethan-1-ol-2-amine acetate is produced by the method of the present invention using o- or p-hydroxyisonitrosoacetophenone as the arylisonitrosoalkanone precursor. To produce 1-(o- or p-hydroxyphenyl)-ethan-1-ol-2-amine acetate, the reaction medium comprises acetic acid in mole equivalent amount at least equal to the mole equivalent of precursor. To produce 1-(o- to p-hydroxyphenyl)-ethan-1-ol-2-acetamide, the reaction medium comprises acetic anhydride or an ester of acetic acid in mole equivalent amount at least equal to mole equivalent of the precursor. Hydrogen is reacted in the presence of a palladium on carbon catalyst. The amount of hydrogen reacted is 3 molar equivalents based on moles of o- or p-hydroxyisonitrosoacetophenone. The hydrogen pressure in the reactor preferably ranges from about 15 psig to about 300 psig. The o- or p-hydroxyisonitrosoacetophenone is suitably present in an amount ranging from about 5% by weight to about 50% by weight of the reaction medium, preferably in an amount ranging from about 5% by weight to about 25% by weight of the reaction medium (the reaction medium excludes the o- or p-hydroxyisonitrosoacetophenone, but includes the palladium on carbon catalyst); the acetic acid, acetic anhydride or ester of acetic acid is suitably present in the reaction medium in an amount ranging from about 10% by weight to about 95% by weight of the reaction medium, preferably from about 40% by weight to about 90% by weight of the reaction medium; and the palladium on carbon catalyst, which typically comprises about 5% by weight to about 10% by weight palladium, is present in an amount such that the palladium present ranges from about 0.005% by weight to about 1.5% by weight of the o- or p-hydroxyisonitrosoacetophenone.

The acylamide or amine acylate salt of the arylalkanolamine of this invention, and most particularly the 1-(o- or p-hydroxyphenyl)-ethan-1-ol-2-acetamide or 1-(o- or p-hydroxyphenyl)-ethan-1-ol-2-amine acetate salt of this invention, is converted in accordance with this invention to the hydrochloride salt of the corresponding arylalkanolamine and in the particular aspect, of 1-(o- or p-hydroxyphenyl)-2-aminoethanol, by reacting the same with hydrogen chloride in a reaction medium comprising a $C_1$-$C_3$ alkyl alcohol, for example, methanol, ethanol or isopropanol.

The arylisonitrsoalkanone employed for the hydrogenation process of this invention may be prepared by 1) reacting a) an arylalkylketone of the formula

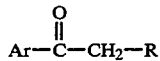

in which R represents hydrogen or a $C_1$-$C_8$ alkyl or cycloalkyl and Ar represents an aromatic phenyl radical unsubstituted, or substituted at the ortho and/or para position, or naphthyl radical unsubstituted or substituted at one or more of the 1, 3, 6, and 7 positions, wherein the substituents, one or more, are selected from the group of hydroxyl, alkoxy, alkyl, phenyl, benzyl, and aryloxy radicals, wherein the alkyl in the alkyl-containing substituent(s) is a branched or unbranched $C_1$-$C_8$ alkyl radical and any such alkyl radical as well as the phenyl and benzyl radicals may be optionally substituted with one or more substituents selected from hydroxyl, sulfonic acid, and sulfinic acid radicals, the phenyl and benzyl substituents also or alternatively being optionally substituted with one or more $C_1$-$C_8$ alkyl or $C_1$-$C_8$ alkoxy, or both, radicals, with b) a lower alkyl nitrite in the presence of hydrogen chloride and in a dipolar aprotic solvent to produce a reaction mixture which includes an arylisonitrosoalkanone reaction product; and 2) combining said reaction mixture with water and extracting the arylisonitrosoalkanone from the aqueous reaction mixture with an organic solvent suitably selected from lower alkyl esters and $C_4$ or higher alkyl alcohols to produce an arylisonitrosoalkanone extract solution.

Examples of arylalkylketones usable in the above described process are those wherein the aryl of the arylalkylketone is an unsubstituted phenyl or naphthyl radical or is a substituted phenyl or naphthyl radical having substitution of the kind previously described. Such arylalkylketones include, but are not limited to, o- and p-hydroxyacetophenone, o- and p-methylacetophenone, p-ethylacetophonone, p-propylacetophenone, p-butylacetophenone, o- and p-methoxyacetophenone, o- and p-ethoxyacetophenone, 2,4-methoxyacetophenone. p-phenylacetophenone, 2-methoxy-4-methylacetophenone, α-acetonaphthone, β-acetonapthone, propiophenone, o- and p-methoxypropiophenone, p-methylpropiophenone, p-ethylpropiophenone, butyrophenone, p-methylbutyrophenone, p-methoxybutyrophenone, valerophenone and p-methylvalerohenone, p-acetamidopropiophenone, p-hydroxyphenylacetophenone, p-hydroxyphenylpropiophenone, 1-(4-methylphenyl)propiophenone, and p-phenylsulfonyl-acetophenone, 4,5 dihydroxy- 1-indanone, 5,6-dihydroxy- 1-indanone, 4,5 dimethoxy-1-indanone and 5,6-dimethoxy-1-indanone.

An arylalkylketone of the above and foregoing formula is reacted with a lower alkylnitrite in the presence of hydrogen chloride in a dipolar aprotic solvent.

The dipolar aprotic solvents employed are solvents which have a high dielectric constant and a high dipole moment but no acid hydrogen atoms; for example, such solvents include dimethylsulfoxide (DMSO), acetonitrile, dimethylformamide (DMF), dimethylacetamide and hexamethylphosphoric acid triamide (HMPT). Suitable alkyl nitrites are lower alkyl nitrites in which the alkyl radical has from 1 to 8 carbon atoms; for example, methylnitrite. ethylnitrite, isopropylnitrite, n-butylnitrite, t-butylnitrite, amylnitrite. n-hexylnitrite. n-heptylnitrite, n-octylnitrite and the like.

The reaction of the ketone with the lower alkyl nitrite suitably can be carried out at a temperature in the range from −30° C. to 100° C., preferably in the range from 10° C. to 50° C. The amount of hydrogen chloride used suitably is from about 0.5 to 5.0 equivalents, relative to the ketone used. Respecting suitable dipolar aprotic solvents and lower alkyl nitrites and conditions for this aspect of the invention, reference is made to U.S. Pat. No. 3,966,813.

Protic by-products of the dipolar aprotic solvents, for example, amine by-products of DMF, interfere with the efficacy or poison the hydrogenation catalysts employed in this invention. Vacuum distillation or differential extraction of the reaction mixture containing the arylisonitrosoalkanone may be used to remove the amine by-product. The reaction mixture is combined with water, preferably ice, and extracted with multiple volumes of an organic solvent in which the arylisonitrosoalkanone is preferentially soluble relative to amines. Suitably the organic solvent is a lower alkyl ester, for example, methylacetate, ethylacetate, propylacetate, or ethanol, propanol, or a $C_4$ or higher alkyl alcohol, for example, n-butanol.

The following examples illustrate the invention, and are not to be understood as limiting the invention only to these embodiments.

EXAMPLE 1

To a 300 ml. Zipperclave (autoclave) is loaded 10 grams (0.0606 moles) of p-hydroxyisonitrosoacetophenone, 12.37 grams (0.1212 moles) of acetic anhydride, 184 ml. of 0.33 molar acetic acid (0.0606 moles) and 3 grams of 5% palladium on carbon. The reactor was sealed, then degassed three times with nitrogen, and then three times with hydrogen. A surge vessel was pressurized to 200 psig with hydrogen, then the reactor was pressurized to 100 pounds with hydrogen. The reaction medium was stirred at about 1250 rpm, and pressure and hydrogen uptake were monitored, hydrogen being added to the reactor during the reaction from the surge vessel. The decrease in hydrogen pressure, initially in the reactor, and then in the surge vessel pressure, indicated hydrogen uptake. The course of the reaction is tabularized below:

TABLE 1

| Time (min.) | Temp. (°C.) | Reactor Pressure (psig) | Surge Vessel (psig) |
|---|---|---|---|
| 0 | 20.6 | 100 | 200 |
| 3 | 28.4 | 50 | 200 |
| 6 | 33.6 | 120 | 196 |
| 11 | 31.0 | 120 | 188 |
| 17 | 29.3 | 120 | 180 |
| 22 | 28.4 | 120 | 178 |
| 32 | 26.5 | 120 | 174 |
| 42 | 25.1 | 120 | 172 |
| 54 | 24.1 | 120 | 172 |
| 63 | 23.1 | 120 | 172 |
| 73 | 23.5 | 120 | 172 |

The product in the reactor at the completion was a concentrated oily residue. Thirty milliliters of the residue was removed and triturated with ethyl ether, and light yellow crystals formed within 5 minutes. The product was then recrystallized with a 10 to 1 molar ratio of ethyl acetate to methyl alcohol, for an 86% yield of the product. Analysis showed the product to be 1-(o- or p-hydroxyphenyl)-ethan- 1-ol-2-acetamide.

EXAMPLE 2

Pure p-hydroxyisonitrosoacetophenone (20 grams) (121 mmol.) was added to a solution containing 400 ml. of 0.33 molar acetic acid (132 mmol.) and 8.2 grams of dry 5% palladium on carbon. The reactor was sealed, then degassed 3 times with nitrogen, then 3 times with hydrogen. The reactor was then pressurized to about 100 psig with hydrogen, with hydrogen being added from a surge vessel during the reaction to maintain pressure at about 100 psig. The reaction medium was stirred at about 1250 rpm. The reaction heated itself to 30° C. (no external heating was used), then the temperature decreased to room temperature as the reaction neared to conclusion.

The course of the reaction is tabularized below. Decrease in surge vessel pressure is an indication of hydrogen consumed:

TABLE 2

| Time (min.) | Temp. (°C.) | Reactor Pressure (psig) | Surge Vessel (psig) |
|---|---|---|---|
| 0 | 26.8 | 100 | 310 |
| 25 | 29.3 | 100 | 225 |
| 38 | 29.9 | 100 | 214 |
| 70 | 30.0 | 100 | 205 |
| 85 | 30.0 | 100 | 205 |

The reaction solution was then filtered to separate the catalyst, and the filtrate was then concentrated under vacuum until crystals of octopamine acetate formed. Recovery was 86%. The octopamine acetate crystals were then treated with 50 ml. of 3.3 molar hydrogen chloride in ethanol. The mixture was warmed to 50° C. and allowed to cool to 5° C., and only then did octopamine hydrogen chloride precipitate out, yielding a 67% recovery.

EXAMPLE 3

α-Isonitrosopropiophenone (5 grams; 0.03 moles), moist 5% palladium on carbon (1 gram), and moist 5% platinum on carbon (1 gram) were dissolved in acetic acid (100 mL) in an autoclave under a blanket of nitrogen. The autoclave was sealed, purged three times with nitrogen and three times with hydrogen. The autoclave was pressurized to 95 psig with hydrogen. Hydrogen was added from a surge vessel during the reaction to maintain the autoclave pressure at 95 psig. The reaction medium was stirred at approximately 1200 rpm, hydrogen pressure and uptake were monitored (Table 3). The reaction was heated after initial hydrogen uptake. After cooling the autoclave, the reaction mixture was filtered to remove the catalysts and stored in the refrigerator. Analysis of the reaction solution by liquid chromatography indicated the formation of phenylpropanolamine (75% based on phenylpropanolamine hydrochloride).

TABLE 3

| Time (min.) | Temp. (°C.) | Reactor Pressure (psig) | Surge Vessel (psig) |
|---|---|---|---|
| 0 | 21.0 | 95 | 389 |
| 25 | 26.2 | 95 | 339 |
| 78 | 25.3 | 95 | 336 |
| 142 | 65.6 | 95 | 321 |
| 365 | 73.5 | 95 | 319 |

The above and foregoing examples are illustrative only, and many variations can be made without departing from the spirit and scope of the present invention as encompassed by the following claims.

What is claimed is:

1. A method of preparing the amine acylate salt of an arylalkanolamine, which comprises the steps of:

a) providing a compound of the formula

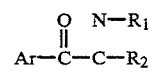

wherein, $R_1$ = an hydroxyl alkyl, or alkyloxy radical $R_2$ = hydrogen or a $C_1$-$C_8$ alkyl or cycloalkyl radical, and Ar = an unsubstituted phenyl radical, or a phenyl radical substituted at the ortho position, the para position, or both the ortho and para positions, or an unsubstituted naphthyl radical, or a naphthyl radical substituted at one or more of the 1, 3, 6, and 7 positions, wherein the substituents are selected from the group consisting of hydroxyl, alkoxy, alkyl, phenyl, and benzyl radicals, wherein the alkyl component is a branched or unbranched $C_1$-$C_8$ alkyl radical, wherein any of said alkyl, phenyl, and benzyl radicals are optionally substituted with one or more substituents selected from amino, hydroxyl, sulfonic acid, and sulfinic acid radicals, and wherein said phenyl and benzyl substituents are optionally substituted with a $C_1$-$C_8$ alkyl or $C_1$-$C_8$ alkoxy radical, or both; and b) reacting said compound with hydrogen in a reaction medium comprising an acyl donor selected from carboxylic acids having a melting point below 100° C. and a hydrogenation catalyst comprising a transition metal catalyst on an inert support, to form a carboxylic acid salt of an arylalkanolamine.

2. The method of claim 1 in which said acyl donor is present in at least one mole equivalent per mole of the compound of the formula of step a).

3. The method of claim 1, in which the hydrogen reacted in step b) is 3 molar equivalents, based on the moles of the compound of said formula of step a).

4. The method of claim 1, wherein the amount of said transition metal present ranges from about 0.005% by weight to about 1.5% by weight of said compound of step a).

5. The method of claim 4, wherein the reaction is carried out under hydrogen pressure ranging from about 15 psig to about 300 psig, at temperatures ranging from about 5° C. to about 100° C.

6. The method of claim 5, wherein said transition metal is selected from the group consisting of platinum, palladium, nickel, rhodium, and combinations thereof.

7. The method of claim 2, in which the acyl donor has a formula of

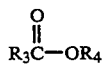

wherein
$R_3$=hydrogen or an alkyl, cycloalkyl, aryl or arylalkyl having from 1 to 10 carbon atoms, and
$R_4$=hydrogen.

8. The method of claim 2, in which the acyl donor is acetic acid or a mixture of acetic acid and acetic anhydride.

9. A method of producing 1-(o- or p-hydroxyphenyl)-1-ethan-1-ol-2-amine-acetate, which comprises the steps of:
   a) providing the compound o- or p-hydroxy-α-isonitrosocetophenone;
   b) reacting said compound with hydrogen in a reaction medium comprising an acyl donor selected from carboxylic acids having a melting point less than 100° C. and a transition metal catalyst on an inert support.

10. The method of claim 9, wherein said acyl donor is present in at least one molar equivalent per mole of said compound of step a).

11. The method of claim 10, wherein in step b) three moles of hydrogen are reacted per mole of said compound of step a).

12. The method of claim 11, wherein said transition metal is selected from the group consisting of platinum, palladium, nickel, rhodium, and combinations thereof.

13. The method of claim 12, wherein said hydrogenation catalyst is palladium.

14. The method of claim 13, wherein said palladium, excluding said inert substrate, is present in a quantity ranging from about 0.005% by weight to about 1.5% by weight based on the weight of said compound of step a).

15. The method of claim 14, wherein the reaction is carried out under hydrogen pressure ranging from about 15 psig to about 300 psig, at temperatures ranging from about 5° C. to about 100° C.

16. The method of claim 15, wherein the o- or p-hydroxyisonitro-soacetophenone is present initially in said reaction medium in an amount ranging from about 5% by weight to about 50% by weight, of said reaction medium, and wherein said palladium on carbon catalyst is present in said reaction medium at a concentration ranging from about 0.01% by weight to about 10% by weight of said reaction medium.

17. The method of claim 16, wherein said o- or p-hydroxyisonitro-soacetophenone is present initially in said reaction medium in an amount less than about 30% by weight of said reaction medium.

18. The method of claim 9 or 17, in which said acyl donor is acetic acid.

* * * * *